United States Patent [19]

Smith et al.

[11] Patent Number: 4,937,269

[45] Date of Patent: * Jun. 26, 1990

[54] MACROPHAGE STIMULATION BY HOMOLOGS OR ANALOGS OF QUADROL

[75] Inventors: Daniel J. Smith, Stow, Ohio; Sanjay R. Patel, Arden, N.C.; Edwin C. Rowland, Athens, Ohio

[73] Assignee: University of Akron, Akron, Ohio

[ * ] Notice: The portion of the term of this patent subsequent to Oct. 18, 2005 has been disclaimed.

[21] Appl. No.: 258,173

[22] Filed: Oct. 14, 1988

Related U.S. Application Data

[63] Continuation-in-part of Ser. No. 901,927, Oct. 20, 1986, Pat. No. 4,778,825.

[51] Int. Cl.$^5$ .............................................. A61K 31/13
[52] U.S. Cl. ..................................... 514/669; 514/667
[58] Field of Search ................................ 514/669, 667

[56] References Cited

U.S. PATENT DOCUMENTS

| | | | |
|---|---|---|---|
| 2,697,118 | 12/1954 | Lundsted et al. | 564/506 X |
| 4,035,480 | 7/1977 | Green et al. | 424/78 |
| 4,290,904 | 9/1981 | Poper et al. | 252/117 X |
| 4,778,825 | 10/1988 | Smith et al. | 514/669 |

FOREIGN PATENT DOCUMENTS 0128476 12/1984 European Pat. Off. .
8806894 9/1988 PCT Int'l Appl. .

OTHER PUBLICATIONS

Chemical Abstracts, vol. 103, 1985, p. 40, Abstract 171653q.

*Primary Examiner*—Leonard Schenkman
*Attorney, Agent, or Firm*—Oldham & Oldham Co.

[57] ABSTRACT

Quadrol and homologs and analogs thereof have been found to stimulate macrophage activity in warm blooded animals. As a consequence, these compounds may be used to combat bacterial infection, remove degenerated tissue, and promote new tissue growth. Quadrol or a homolog or analog thereof may be applied topically, e.g., as the active agent in a wound dressing. The active compounds may be represented by the formula (I)

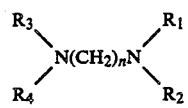

wherein $R_1$ and $R_2$ are substituted alkyl ($C_2$–$C_6$) in which the substituents include one or more hydroxyl groups attached to carbon atoms other than the alpha carbon atom, $R_3$ and $R_4$ are alkyl or substituted alkyl ($C_1$–$C_6$), and n=2 to about 6. Preferably $R_1$ through $R_4$ are the same and are 2-hydroxyalkyl.

28 Claims, No Drawings

MACROPHAGE STIMULATION BY HOMOLOGS OR ANALOGS OF QUADROL

CROSS REFERENCE TO RELATED APPLICATION

This application is a continuation in-part of our co-pending application Serial No. 901,927, Filed Oct. 20, 1986 now U.S. Pat. No. 4,778,825.

TECHNICAL FIELD

This invention relates to methods and agents for stimulating macrophage activity in warm blooded animals, including man.

BACKGROUND ART

Macrophages, or large phagocytes, are important in wound healing, fighting infection in a variety of immune responses in warm blooded animals including man. They promote the wound healing process in various ways. For example, macrophages engulf and destroy bacteria and degenerating tissue. They also kill intracellular pathogens. They also appear to secrete and release factors which promote the growth of new collagen. Macrophages are found in the blood stream and in various tissues including the liver and the peritoneum.

Macrophages can be specifically activated as a part of the cellular immune response by various materials including immune complexes, compliment components, lymphokines and tuftsin. Other macrophage stimulation agents include lipopolysaccharides (LPS), muramyl dipeptide, physiologic cation complexing agents such as certain pyran copolymers and other polycarboxylates, and certain ionophores.

Administration of a macrophage stimulating agent to a host animal increases the activity of macrophages in the host, so that they more effectively perform their various functions. These various functions are known in the art, and some of these functions have been described above. In particular, administration of a macrophage stimulating agent to a wound site in a host animal stimulates macrophages in the host so that they more effectively perform the various healing functions, some of which have been discussed above.

The majority of known macrophage stimulators are macromolecular in nature. Most of them are naturally occurring materials or derivatives of naturally occurring materials, and most are quite expensive. Pyran copolymers are among the few known synthetic macrophage stimulating agents.

Quadrol, N,N,N',N'-tetrakis(2-hydroxypropyl)etylenediamine is a known compound having the structural formula (I-a)

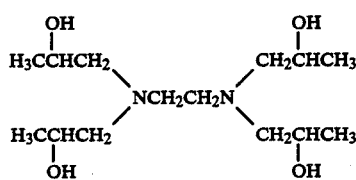

Quadrol can be synthesized by reacting 1 mole of ethylenediamine with 4 moles of propylene oxide, as described for example in U.S. Pat. No. 2,697,113 to Lundsted et al. Quadrol is known to complex a number of polyvalent cations such as $Co^{2+}$, $Cu^{2+}$, and $Zn^{2+}$ and has been used as an analytical reagent for the determination of trivalent manganese ($Mn^{+++}$) in solution. Quadrol is often used as a cross-linking agent and catalyst in the synthesis of polyurethane foams and membranes.

It is an object of this invention to provide an inexpensive and non-toxic agent having macrophage stimulation activity.

It is a further object of this invention to provide wound dressings which incorporate an inexpensive, non-toxic macrophage stimulating agent.

According to this invention, macrophage cell activity in a warm blooded animal is promoted by administering Quadrol to said animal.

BEST MODE FOR CARRYING OUT INVENTION

Applicants have discovered that compounds of the formula (I)

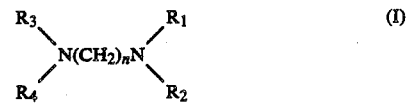

wherein:
R₁ and R₂ may be the same or different and each is a substituted alkyl radical containing from 2 to about 6 carbon atoms and in which the substituents include one or more hydroxyl groups attached to carbon atoms other than the alpha carbon atom, R₃ and R₄ may be the same or different and each is alkyl or substituted alkyl radical containing from 1 to about 6 carbon atoms, and n is from 2 to about 6 are biologically active. In particular, these compounds have macrophage stimulating activity. In addition, these compounds are virtually non-toxic. These compounds are particularly useful as the (or an) active ingredient of wound dressings.

Preferred compounds of formula (I) are those in which R₁, R₂, R₃ and R₄ are 2-hydroxyalkyl radicals. These groups may be the same or different but are preferably the same for ease of synthesis. It is preferred that the hydroxyl group be at the 2- (or beta-) position rather than at a more remote position, both for improved biological activity and ease of synthesis. Similarly, a hydroxyl group is preferably at the 2- position rather than at the 1- (or alpha-) position. For maximum activity it is preferred that the 1- position be unsubstituted, i.e., that a —CH₂— group be present at this position.

R₁, R₂, R₃, and R₄ may each contain more than one hydroxyl group. In this case, one hydroxyl group is preferably at the 2-position and the other hydroxyl group(s) is (are) at more remote position(s).

When either R₃ or R₄ is alkyl (as opposed to hydroxyalkyl), it is preferred that the alkyl group contain no more than 3 carbon atoms so that the compound of formula (I) will be hydrophilic. This is particularly true when both R₃ and R₄ are alkyl.

Substituents other than hydroxyl may be present in R₁, R₂, R₃ and R₄ provided that the substituent has no appreciable adverse effect on either activity or toxicity. In particular, chloro- and bromo- substituents may be present. However, no advantage is gained by the presence of substituents other than hydroxyl, as far as applicants are aware.

Use of the compound Quadrol (compound I-a), which is the compound of formula (I) wherein $R_1=R_2=R_3=R_4=$2-hydroxypropyl and $n=2$, is the subject of applicants' copending U.S. Pat. application Ser. No. 06/901,927, filed Oct. 20, 1986. The present application is particularly directed to methods employing homologs and/or analogs of Quadrol, i.e., to compounds of formula (I) with the proviso that n is from 3 to about 6 when $R_1=R_2=R_3=R_4$ and each is 2-hydroxypropyl, and to wound dressings employing such compounds.

Compounds of formula (I) wherein $R_1$ through $R_4$ are all 2-hydroxypropyl and n is from 2 to about 6 can be prepared by reacting the appropriate aliphatic diamine (preferably a straight chain alpha,omega aliphatic diamine) such as ethylenediamine, 1,3-diaminopropane, 1,4-diaminobutane, etc, with propylene oxide according to the method described in U.S. Pat. No. 2,697,113 cited supra. This method can also be used to prepare other 2-hydroxyalkyl compounds of formula (I) in which $R_1$, $R_2$, $R_3$ and $R_4$ are the same, by reacting a straight chain aliphatic diamine with a 1,2-epoxyalkane, e.g., ethylene oxide, 1,2-epoxybutane, etc. It is preferred to use a 1,2-epoxyalkane rather than an epoxyalkane in which the oxygen atom is not attached to a terminal carbon atom such as 2,3-epoxybutane for example, because the latter will introduce a lower alkyl group at the 1-position of $R_1$, $R_2$, $R_3$ and $R_4$. It is preferred that the 1-position be unsubstituted as previously noted.

An epoxyalkanol, such as glycidol, is substituted for the epoxyalkane in the above synthesis when a compound of formula (I) in which $R_1$, $R_2$, $R_3$ and $R_4$ are dihydroxyalkyl radicals is desired. The compounds thus obtained are novel. One hydroxyl radical is in the 2-position and the other in the 3- or more remote position (the 3-position when glycidol is used).

Compounds of formula (I) in which $R_4$ is alkyl and $R_1$, $R_2$ and $R_3$ are the same 2-hydroxyalkyl radical can be prepared by reacting one mole of an aliphatic diamine successively with one mole of an alkyl halide (i.e., chloride or bromide) such as methyl bromide, ethyl bromide or propyl bromide, and with 3 moles of a 1,2-epoxyalkane such as propylene oxide. These two steps can be performed in either order.

Compounds in which both $R_3$ and $R_4$ are lower alkyl and $R_1$ and $R_2$ are 2-hydroxyalkyl require a reaction sequence which includes blocking of both hydrogen atoms attached to one nitrogen atom, alkylation, deblocking and epoxidation. Blocking can be carried out according to the method of R. West et al, Journal of the American Chemical Society, vol. 90, no. 3, 1968, pages 727–731. This article describes preparation of N,N-bis(-trimethylsilyl)ethylenediamine from ethylenediamine in 3 steps. Subsequent alkylation (e.g., with a lower alkyl halide such as methyl bromide), deblocking (e.g., with methanol or water) and epoxidation (with a 1,2-epoxyalkane such as propylene oxide) using reaction conditions known in the art yields a compound of the formula (I) in which $R_1$ and $R_2$ are the same 2-hydroxyalkyl radical (e.g. 2-hydroxypropyl) and $R_3$ and $R_4$ are the same lower alkyl radical (e.g., methyl). The order of the last 3 steps can be changed, e.g., epoxidation, deblocking and alkylation (with the same reactants as mentioned before) in that order. It will also be apparent that this appropriate straight chain aliphatic diamine, e.g., 1,3-diaminopropane, 1,4-diaminobutane, etc., can be substituted for ethylenediamine to give compounds in which n is 3 to 6.

To introduce a hydroxyalkyl radical having a gamma (or 3-) hydroxyl group, one reacts one mole of ethylenediamine or other straight chain aliphatic ($C_3$–$C_6$) diamine with 4 moles of a halo-substituted aliphatic ketone such as 4-chloro-2-butanone (the halogen is preferably Cl or Br and is preferably in the omega position), followed by reduction, e.g., with lithium aluminum hydride, hydroxyl substituents at positions more remote than the 3-position can be prepared similarly, using 5-chloro-2-pentanone or 6-chloro-2-hexanone, for example. Alternatively, one can react an aliphatic diamine with a halo-substituted secondary alcohol (4-chloro-2-butanol, for example) instead of the corresponding ketone; no reduction step is required in this instance. However, the preferred compounds of formula (I) are those in which $R_1$ and $R_2$ (and preferably $R_3$ and $R_4$ as well) are 2-hydroxyalkyl, both for activity and ease of synthesis.

Compounds in which $R_1$ and $R_2$ are different, or in which $R_3$ and $R_4$ an different (other than $R_3=$hydroxyalkyl and $R_4=$alkyl) can be prepared but are more complex to prepare than compounds in which $R_1$ and $R_2$ are the same and $R_3$ and $R_4$ are the same, and do not offer any advantages in terms of activity as far as is known.

Macrophage stimulation activity of certain compounds of formula (I), as for example Quadrol (I-a; $R_1=R_2=R_3=R_4=$2-hydroxypropyl, $n=2$), and homologs and analogs thereof as illustrated in Examples 7 to 14, has been demonstrated in vitro using standard test methods, which will be described in greater detail in the examples. Quadrol has also been demonstrated to have macrophage activity in vivo. The stimulatory effect of these has been found to be both concentration and time dependent in both in vitro and in vivo experiments.

Compounds of formula (I) may be administered topically to an animal in need of treatment for infection or other condition which responds to macrophage stimulation. The compound may be administered as a composition of matter comprising said compound and a suitable pharmaceutically acceptable carrier, particularly a solid or semisolid (e.g., paste) carrier in which the compound is insoluble. When the compound is applied topically to a wound, lesion or sore in a warm blooded animal, including man, the compound stimulates the activity of macrophages at the site of the wound, lesion or sore. The macrophages, in turn, promote the healing process, e.g. by engulfing and destroying bacteria and degenerating tissue, by promoting closure of the wound or lesion, and by promoting the growth of new tissue. These compounds are potentially particularly valuable agents for the treatment of wounds and sores which either do not heal or which heal very slowly when treated according to presently known methods. Wounds and sores heal very slowly in diabetics, for example, and these compounds appear to be potentially valuable agents for promoting the healing of wounds and sores in such patients.

According to a particularly preferred embodiment of this invention, a wound dressing containing a homolog or analog of Quadrol as the biologically active agent is prepared and applied to a skin wound or lesion of the host animal. The wound dressing may comprise a standard bandage material, e.g. gauze, impregnated with an aqueous solution of Quadrol homolog or analog having a concentration ranging from about 1 to about 40 millimolar (mM). All or a portion of the bandage material may be so impregnated. Preferably, however, a pharmaceutically effective amount of Quadrol homolog or analog is incorporated into an ointment, which in turn is applied to the portion of the bandage which is placed over the wound or lesion. The ointment base may be conventional and is preferably of paste consistency. The amount of Quadrol homolog or analog may be approximately 0.1 to 0.4 percent of the total ointment weight. The bandage is then applied to the skin wound or lesion in a conventional manner. Of course, when the bandage is only partially impregnated with a homolog or analog of Quadrol, the impregnated portion must be placed over the wound site.

While a conventional bandage material is the preferred support or carrier for topical administration, the homolog or analog of Quadrol may be absorbed on other pharmaceutically acceptable supports or carriers, a polymer membrane for example, and applied to a skin wound or lesion.

Wound dressings impregnated with a homolog or analog of Quadrol according to this invention promote the wound healing process in a variety of ways, as indicated above, by stimulating the macrophage cells of the host animal. In contrast, the presently known wound dressings merely protect the wound from infection and foreign matter and, when a therapeutically active agent is present, reduce infection by attacking bacteria without assisting the healing process in other ways, as for example by destruction and removal of dead or degenerating tissue, or by promoting the growth of new collagen.

For minor wounds, the active compound may be applied topically in the form of a paste or ointment. Such paste or ointment may comprise a homolog or analog of Quadrol and other conventional pharmaceutically acceptable paste or ointment ingredients.

Quadrol itself may be used in the same manner as a homolog or analog thereof in wound dressings as described above.

Compared to other known stimulators of macrophage spreading and phagocytosis, Quadrol and its homologs and analogs are unusual in that they are synthetic, of low molecular weight, and inexpensive. The low cost is a major advantage, particularly in the case of intractable wound infections which require repeated administration over a period of a number of days.

This invention will now be described further with reference to the examples which follow. Example 1 shows that macrophage cells retain their viability at Quadrol concentrations far above those required for effective macrophage stimulation. Examples 2, 3, 4 and 6 represent standard in vitro tests (or minor modifications thereof) used to show macrophage stimulation activity. Example 5 shows that Quadrol is an effective macrophage stimulator in vivo: it also shows that Quadrol retains its activity when bonded to a solid support or carrier. This is important because Quadrol is water soluble, and can be effective over a much long period of time in an insolublized form. Examples 7 to 14 describe preparation of homologs and analogs of Quadrol (all of which are compounds of formula I). Example 15 describes in vitro macrophage testing of the compounds of Examples 7 to 14.

EXAMPLE 1

Macrophage Cell Viability In Vitro

Six to eight week old mice were used as a source of resident peritoneal exudate cells. After asphyxiation of the mice by $CO_2$, the peritoneal cavity was washed with Alsever's solution. The cells were collected, washed three times with PBS (phosphate buffered saline solution, 0.01 M, pH 7.2), and resuspended in Eagle's minimum essential medium (EMEM), pH 7.2, supplemented with 10 percent heat inactivated fetal bovine serum, 1 percent glutamine (200 mM), 100 units/mL penicillin, and 100mg/L streptomycin (hereinafter "supplemented EMEM"), to a concentration of $2 \times 10^6$ cells/mL. This cell suspension (hereinafter "cell suspension") was used in all assays.

Quadrol solutions for testing in all examples were prepared as follows: Quadrol was dissolved in 10mM phosphate buffered saline solution (PBS) and adjusted to pH 7.1 with sodium hydroxide or hydrochloric acid to make 5mM, 20mM, 40mM, 60mM and 160mM stock solutions. These stock solutions were diluted with supplemented EMEM to make 0.5mM, 1mM, 4mM, 16mM and 32 mM test solutions.

To assay macrophage viability after incubation with Quadrol, Leighton test tubes, containing either cell suspension ($2 \times 10^6$ cells/mL) (control) or a test suspension prepared by mixing 0.1mL each of cell suspension and one of the stock solutions of Quadrol described above, were incubated at 37° C. in a humid environment containing 5 percent (by volume) $CO_2$ and having relative humidity of 100 percent. (This same composition was used throughout the examples wherever a humid environment is called for, and the term "$CO_2$-containing humid environment" when used hereafter denotes an environment of this composition). Incubation times were 1 hour, 2 hours, 4 hours, 6 hours and 24 hours. At each time interval, test tubes were removed from the incubator and 0.3mL of the cell suspension was taken out of each test tube and placed in a small siliconized test tube. Trypan blue dye solution (0.1mL) was added and mixed gently for 5 minutes to allow sufficient time for the dead cells to take up the dye. Slides of each cell suspension were prepared by layering a portion of the suspension onto a clean glass coverslip and examined with a light microscope and the number of live and dead cells was counted. Viability (in percentage terms) is calculated by dividing the number of live cells counted by the total number of cells counted, a multiplying by 100.

Results are shown in Table I. This Table shows the percentage of viable cells for the control and for each Quadrol solution concentration tested at each incubation time tested. Results represent averages of 7 identical experiments.

TABLE I

| | Percentage of Viable Cells | | | | |
|---|---|---|---|---|---|
| | Incubation time, hours | | | | |
| | 0.5 | 1 | 2 | 4 | 6 |
| Quadrol concentration | | | | | |
| 0.5 mM | 93 | 90 | 90 | 85 | — |
| 1 mM | 89 | 92 | 91 | 92 | 88 |
| 4 mM | 79 | 72 | 67 | — | 64 |
| 16 mM | 88 | 74 | 67 | 63 | 51 |
| Control | 92 | 92 | 88 | 92 | 88 |

Results with 0.5mM and 1mM Quadrol showed no significant difference of the control in cell viability. Quadrol concentrations of 4mM and 16mM, on the other hand, significantly reduced cell viability; cell viability in cells incubated for 6 hours in a 16mM Quadrol solution had only half the viability of cells incubated in the control medium for a similar length of time.

EXAMPLE 2

Macrophage Spreading In Vitro

Samples of cell suspension (0.100mL each) were layered on to clean glass coverslips (#2, Corning Glass Co.) and incubated for 30 minutes at 37° C. in a $CO_2$-containing humid environment. After incubation the coverslips were washed to remove nonadherent cells, then covered with 0.mL of either a Quadrol test solution, LPS (lipopolysaccharide buffered to pH 7.2) 20 mg/L or supplemented EMEM (control). All solutions and suspensions applied to coverslips were adjusted to a pH of about 7.1–7.2 to avoid acid induced spreading. Incubation times were 1 hour, 2 hours, 4 hours, 6 hours and 24 hours. At the end of each incubation period, the coverslips were washed with warm PBS and fixed by the addition of 2 percent glutaraldehyde, pH 7.2, prewarmed to 37° C. After 5 minutes, the coverslips were washed with 0.1M sodium cacodylate buffer and examined under a Zeiss phase contrast microscope at 400× magnification. Both normal and spread cells were counted. Spread cells appeared gray and had an extended apron or diameter, whereas the unspread (normal) cells were rounded and refractile. Approximately 400 cells were counted per coverslip. Seven experiments were carried out for each concentration and incubation time tested.

Table II below shows the effect of Quadrol on macrophage spreading as a function of incubation time and concentration. In Table II below, "% Spreading" indicates the percentage of cells which had spread.

TABLE II

| Solution | % Spreading Time, Hours | | | | |
|---|---|---|---|---|---|
| | 1 | 2 | 4 | 6 | 24 |
| Quadrol: | | | | | |
| 1 mM | 22 | 45 | 88 | 92 | 93 |
| 4 mM | 22 | 34 | 81 | 70 | 69 |
| 16 mM | 10 | 15 | 60 | 41 | 40 |
| LPS | 31 | 37 | 67 | 67 | 69 |
| Control | 20 | 26 | 28 | 30 | 35 |

As shown in Table II, the increase in macrophage spreading was linear with time with a maximum achieved at 4 hours for all solutions tested (except the 1mM Quadrol solution and the control, where slight further increases in spreading after 4 hours were noted). After 4 hours, concentrations of 1mM and 4mM Quadrol produced enhanced spreading of 88 percent in the control. In fact, spreading values exceeded those obtained with LPS, which is a known macrophage stimulating agent. Quadrol concentrations at 16mM showed less stimulatory effect than either LPS or the 1mM, 4mM Quadrol solutions; however, this is not of practical interest since data in Example 1 show that Quadrol at 16mM concentration has an adverse effect on cell viability. Consequently, use of Quadrol in lower concentrations in indicated.

EXAMPLE 3

Bead Phagocytosis by Macrophages In Vitro

Effect of Dosage

The degree of macrophage phagocytosis in this example is an indication of the extent of macrophage stimulation activity. A greater percentage of phagocytosis indicates a greater stimulation of macrophage activity. The bead phagocytosis assay for resident peritoneal macrophages described in this exampled was modified from Dunn et al, "Limphokine-Stimulated Macrophage Phagocytosis of Fluorescent Microspheres: A Rapid New Assay", *J. Immunol. Methods*, 64:71, 1983.

Solutions tested in this example were Quadrol (1.0mM and 4.0mM) (prepared as described in Example 2), and supplemented EMEM, (control). Doses of tuftsin and LPS used in this example are known to be stimulatory.

Cell suspensions (75 μL each) were layered onto clean coverslips and incubated for 60 minutes at 37° in a $CO_2$-containing humid environment. After washing with PBS buffer, 25 μL of solution to be tested and 25 μL of suspension of polystyrene beads 3 μ in diameter, in supplemented EMEM (2.55×10beads/mL medium) were added to each coverslip. Following incubation for 45 minutes at 37° in a $CO_2$-containing humid environment, the coverslips were washed with PBS, fixed using 2 percent glutaraldehyde, and stored in 0.1M sodium cacodylate buffer. Five replicate coverslips were used for each solution tested in each experiment. Wet mounts of the coverslips were prepared and observed under a Zeiss phase contrast microscope at 400× to 1000×. Cells with 2 or more beads within the outline of the cell membrane and in the same focal plane were considered as phagocytizing cells. Approximately 300–400 cells per coverslip were observed. The percentage phagocytosis was determined by counting both phagocytizing and non-phagocytizing cells, and dividing the former by the total and multiplying by 100.

Results are shown in Table III.

TABLE III

| Solution | Phagocytosis (%) |
|---|---|
| Quadrol: | |
| 1 mM | 41 |
| 4 mM | 57 |
| Tuftsin | 53 |
| LPS | 64 |
| Control | 34 |

Results in Table III represent mean values obtained in five identical experiments for each solution tested. The standard error in each case is about plus or minus 4 percent.

Results in this example show that Quadrol in either 1 or 4mM concentration has a macrophage stimulating effect. The effect of 4mM Quadrol exceeds that of Tuftsin, a known macrophage stimulating agent tested at a known stimulatory concentration.

EXAMPLE 4

Bead Phagocytosis by Macrophages in Vitro

Effect of Time

Solutions tested in this example were Quadrol (4mM), LPS and control (supplemented EMEM).

The procedure of Example 3 was followed, except that the test solutions were those indicated in the preceding paragraph and the incubation times of the test solutions and bead suspensions were 5 minutes, 15 minutes, 30 minutes and 45 minutes.

TABLE IV

| Solution | Incubation time (minutes) | | | |
|---|---|---|---|---|
| | 5 | 15 | 30 | 45 |
| Quadrol (4 mM) | 63 | 70 | 71 | 68 |
| LPS | 60 | 68 | 76 | 63 |

TABLE IV-continued

| Solution | Incubation time (minutes) | | | |
|---|---|---|---|---|
| | 5 | 15 | 30 | 45 |
| Control | 4 | 47 | 55 | 48 |

Each value shown in Table IV represents the means of five identical experiments. The standard error in each case is in the range of plus or minus 2 to 3 percent.

Data in Table IV show that stimulation of macrophage phagocytic activity reached a peak at 30 minutes and thereafter declined. Data also show that there were no significant differences in the activity of Quadrol (4mM) and LPS at any incubation time tested and that both exhibited far greater phagocytosis than did the control.

EXAMPLE 5

Macrophage Stimulation In Vivo

Balb/c mice 6 to 8 weeks old (3 per group) were injected intraperitoneally with 0.2mL of a suspension of PBS containing 35 mg glass beads with Quadrol covalently attached, 35 mg glass beads alone or PBS alone.

The glass beads as purchased were microporous beads (pore diameter 50nM; purchased from Pierce Chemical Co.) having a long chain alkyl amine bonded thereto. Quadrol was bonded to the beads by first swelling the beads in toluene, then treating them with diphenylmethane diisocyanate (MDI) in toluene under conditions such that only one isocyanate group reacted with the amine group, then further treating the beads with Quadrol in the presence of a catalyst under conditions such that only one hydroxyl group of the Quadrol reacted with only one hydroxyl group of the Quadrol reacted with the isocyanate group to form the desired covalent linkage. Finally, the beads were soaked in methanol for 24 hours and oven dried under vacuum.

Three days after injection, the mice were sacrificed and their peritoneal exudate cells were then placed on coverslips for determination of spreading. (The criteria for determining the percent of cell spreading are described in Example 2). After 1 hour of incubation at 37° C., the coverslips were washed, fixed with glutaraldehyde and examined microcopically. The percentage of spreading of macrophage cells on each coverslip is indicated in Table V below.

TABLE V

| Mice Injected With | % Spreading |
|---|---|
| Quadrol on glass beads | 43.1 |
| Glass beads | 18.2 |
| PBS | 14.1 |

This example shows that Quadrol retains its macrophage stimulating activity even when bonded to a solid support. It also shows that Quadrol is effective in vivo.

EXAMPLE 6

Glucose Utilization

Six to eight week old balb/c female mice were used as the source of peritoneal exudate cells. The mice were injected with sterile thioglycollate (1.5mL). Four days later, the mice were asphyxiated and the cells harvested and washed with PBS as described in Example 1.

Peritoneal cells were suspended in supplemented EMEM containing N-2-hydroxyethylpiperazine-N'-2-ethanesulfonic acid (HEPES)(25mM). (The composition of supplemented EMEM is described in Example 1). Portions of the cell suspension (0.2mL each) were placed in flat bottomed, 96-well plates (Corning No. 25860) and incubated for 2 hours at 37° in a CO2 containing-humid atmosphere. Non-adherent cells were removed by washing with EMEM. Test suspensions were prepared by mixing equal volumes of the cell suspension described in this example with Quadrol 1mM and Quadrol 4mM stock solutions prepared as described in Example 1. The cell suspension described earlier in this example (with no added Quadrol) served as the control. Each of the resulting suspensions was incubated for 24, 48 and 72 hours and the percentage of glucose remaining in each suspension at each time interval was measured using a Sigma #5-10 glucose kit. The amount of glucose remaining is reported in Table VI. Also reported in Table VI is the percentage of uptake enhancement, which is calculated as shown below:

$$\% \text{ Uptake} - 100 = \% \text{ Remaining} \quad (1)$$

$$\% \text{ Enhancement} = \frac{\% \text{ Uptake in Test}}{\% \text{ Uptake in Control}} \times 100 \quad (2)$$

TABLE VI

| | % Glucose Remaining and % Uptake Enhancement | | | | | |
|---|---|---|---|---|---|---|
| | % Glucose Remaining Time, Hrs. | | | % Uptake Enhancement Time, Hrs. | | |
| | 24 | 48 | 72 | 24 | 48 | 72 |
| Quadrol Concentration | | | | | | |
| 1 mM | 78 | 57 | 42 | 22 | 34 | 16 |
| 4 mM | 71 | 41 | 28 | 61 | 84 | 44 |
| Control | 82 | 68 | 50 | 0 | 0 | 0 |

The above results show that utilization, or uptake of glucose, is enhanced considerably by a 4mM Quadrol test solution, and much less so by a 1mM Quadrol test solution.

EXAMPLE 7

N,N,N',N',-Tetrakis(2-hydroxypropyl)1,3-diaminopropane (I-b)

Synthesis: Propylene Oxide (37.3g, 0.64mol) was added to a solution of 1,3 diaminopropane (8.8g, 0.1187mol) in 2mL of 50% ethanol. The reaction mixture was contained in a two neck flask with an attached dry ice condenser and maintained at 90° C. for 6 hr. After concentration in vacuo, the resultant oil was dissolved in ether and dried over anhydrous sodium sulfate. Filtration and concentration in vacuo produced a colorless oil (34.36g) in 94.47% yield. Further purification was accomplished by taking the product in ethanol and passing anhydrous HCl gas into the solution to obtain a hydrochloride salt of the quadrol derivative. The crystals were recrystallized in hot ethanol. Crystals were taken up in dilute aqueous KOH (pH 12-13). The derivative was extracted with methylene chloride, dried, filtered and concentrated to obtain a viscous oil which on storage crystalline.

Anal. Calcd for $C_{15}H_{34}N_2O_4 \cdot \frac{1}{4} H_2O$: C, 57.94; H, 11.02; N, 9.00. Found: C, 58.03; H, 10.92; N, 8.99.

EXAMPLE 8

N,N,N',N',-Tetrakis(2-hydroxypropyl)-1,4-diaminobutane (I-c)

Synthesis: Propylene Oxide (34.67g, 0.597mol) was added drop wise to 1–4 diaminobutane (8.7g, 0.099mol) in 1.4ml $H_2O$ and 0.2ml triethyamine at 55° C. After complete addition of propylene oxide the temperature was raised to 70° C. and reaction was allowed to continue for another 3–4hr. After concentration in vacuo. The resultant oil was taken up in ether and dried over anhydrous sodium sulfate. Filtration and concentration in vacuo. produced a colorless oil (30.10g) in 94.8% yield. Further purification by passing anhydrous HCl into an ethanol solution of I-c was attempted but salt precipitation did not occur.

Anal. Calcd for $C_{16}H_{36}O_4N_2 \cdot \frac{1}{2} H_2O$: C, 58.32; H, 11.01; N, 8.50 Found: C,58.41; H, 11.52; N, 8.51.

EXAMPLE 9

N,N,N',N',-Tetrakis(2-hydroxybutyl) ethylenediamine (I-d)

Synthesis: 1,2- Epoxybutane (51.35g, 0.71mol,) was added dropwise to a solution of ethylenediamine (7.12g, 0.12mol) in 2mL of 50% ethanol. The reaction mixture was contained in a three necked flask with an attached dry ice condenser and maintained at 90° C. for 6 hr. After concentration in vacuo the resultant oil was dissolved in ether and dried over anhydrous sodium sulfate. Filtration and concentration in vacuo produced a colorless oil (40.9g) in 99.1% yield.

Further purification by passing anhydrous HCl did not form a salt precipitate. Anal. Calcd for $C_{18}H_{40}N_2O_4$. C, 62.08; H, 11.56; N, 8.03; Found: C, 62.03; H, 11.27; N, 8.03.

EXAMPLE 10

N,N,N',N',-Tetrakis(2-hydroxybutyl)-1,3-diaminoorooane (I-e)

Synthesis: 1,2 Epoxybutane (51.35g, 0.711mol) was added dropwise to 1,3 diaminopropane (8.8g, 0.12mol) in 1.8ml $H_2O$ and 0.2ml triethylamine at 55° C. After complete addition of epoxybutane the temperature was increased to 70° C. and maintained for 4 hrs. in accordance with procedure given in Example 8. The product a colorless oil, was obtained (41.8g) in 97.3% yield. Anal. Calcd for $C_{19}H_{42}N_2O_4$; C, 62.94; H, 11.67; N, 7.72; Found: C, 62.64; H, 11.50; N, 7.78.

EXAMPLE 11

N,N,N',N',-Tetrakis(2-hydroxybutyl)-1,4-diaminobutane (I-f)

Synthesis: Epoxybutane (42.85g, 0.59mol) was added dropwise to 1,4-diaminobutane (8.7g, 0.10mol) in 1.8ml $H_2O$ and 0.2ml triethylamine in accordance with the procedure outlined for the synthesis given outlined in Example 8. The product, a colorless oil was obtained (36.5g), in 98.1% yield.

Elemental Analysis:

Calcd for $C_{20}H_{44}N_2O_4 \cdot \frac{1}{4} H_2O$; C, 63.03; H, 11.63; N, 7.35; Found: C, 62.89; H; 11.73; N, 6.93

EXAMPLE 12

N,N,N',N',-Tetrakis(2,3-dihydroxypropyl) ethylenediamine (I-g)

Synthesis: Glycidol (6.0g, 0.08mol) was added very carefully to ethylenediamine (1.0g, 0.016 mol) in 2ml ethanol in a single neck flask kept on ice. After addition the flask was closed and the reaction was run overnight at room temperature. The reaction product was washed thoroughly well with chloroform and then concentrated in vacuo to remove excess glycidol and ethanol. The product, a very viscous colorless oil (4.68g) was obtained in 98.7% yield.

Elemental Analysis: Anal. Calcd for $C_{14}H_{32}N_2O_8 \cdot \frac{1}{4} H_2O$; C, 46.59; H, 8.93; N, 7.76; Found: C, 46.41; H, 9.29; N, 7.20.

EXAMPLE 13

N,N,N',N',Tetrakis (2,3-dihydroxypropyl) 1.3-diaminopropane (I-h)

Synthesis: Glycidol (6.0g, 0.08mol) was added carefully to a mixture of 1,3 diaminopropane (1g, 0.013mol) in 2ml ethanol following the procedure of Example 12. After purification a colorless oil product (4.75g) in 97.9% yield was obtained.

Elemental Analysis: Anal. Calcd for $C_{15}H_{34}N_2O_8 \cdot \frac{1}{2} CH_3CH_2OH$; C, 45.78; H, 8.7; N, 7.1; Found: C, 45.05; H, 9.07; N, 6.74.

EXAMPLE 14

N,N,N',N',-Tetrakis(2,3-dihydroxypropyl 1,4 diaminobutane (I-i)

Glycidol (4.0g, 0.05mol) was added to 1,4-diaminobutane (1.0g, 0.011mol) in accordance with the procedure of Example 12. A colorless, viscous oil was obtained (4.30g), in 98.9% yield.

Elemental Analysis: Calcd for $C_{16}H_{36}N_2O_8$; C, 49.98; H, 9.43; N, 7.28; Found: C, 49.65; H, 9.43; N, 7.01.

Example 15

Macrophage testing in vitro

Macrophage stimulation activity of compounds I-a (Quadrol) and compounds I-b to I-i (the compounds prepared according to Examples 7 to 14, respectively) was tested using the bead phagocytosis assay described in Example 3. The tests were carried out in 3 series, designated A, B and C; each series included tests of a control (no active compound), Quadrol and either 2 or 3 test compounds (I-b through I-i). Different test animals were used for each series. All tests were carried out at the concentration of 4mM of test compound. The minor differences in observed phagocytosis values of the control and Quadrol are attributable primarily to differences in response among the different test animals used. Results are shown in Table VII below:

TABLE VII

| Compound | Phagocytosis % Series | | |
| --- | --- | --- | --- |
|  | A | B | C |
| Control | 46.4 | 49.1 | 48.6 |
| Quadrol (I-a) | 68.3 | 73.8 | 63.3 |
| I-b | 73.1 | — | — |
| I-c | 70.4 | — | — |
| I-d | — | 71.4 | — |
| I-e | — | 68.2 | — |
| I-f | — | 76.6 | — |
| I-g | — | — | 56.0 |

TABLE VII-continued

| Compound | Phagocytosis % Series | | |
|---|---|---|---|
| | A | B | C |
| I-h | — | — | 61.2 |
| I-i | — | — | 56.9 |
| LPS | 74.5 | — | — |

While in accordance with the patent statues, a preferred embodiment and best mode has been presented, the scope of the invention is not limited thereto, but rather is measured by the scope of the attached claims.

What is claimed is:

1. A method of promoting healing of a wound in a warm blooded animal by stimulating macrophage cell activity at the wound site, which comprises applying to said wound site a composition comprising a pharmaceutically effective amount of a compound of the formula (I)

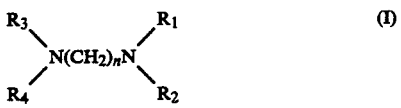

wherein:
 $R_1$ and $R_2$ may be the same or different and each is a substituted alkyl radical containing from 2 to about 6 carbon atoms and in which the substituents include one or more hydroxyl groups attached to carbon atoms other than the alpha carbon atom,
 $R_3$ and $R_4$ may be the same or different and each is an alkyl or substituted alkyl radical containing from 1 to about 6 carbon atoms, and
 n is from 2 to about 6;
and a pharmaceutically acceptable carrier.

2. A method according to claim 1 with the proviso that n is from 3 to about 6 when $R_1=R_2=R_3=R_4$ and each is 2-hydroxypropyl.

3. A method according to claim 1 wherein n is from 3 to about 6.

4. A method according to claim 1 wherein n is 3 or 4.

5. A method according to claim 1 with the proviso that $R_1$ and $R_2$ contain a maximum of 3 carbon atoms when no hydroxyl group is present.

6. A method according to claim 1 in which $R_1$ and $R_2$ are each monohydroxyalkyl or dihydroxyalkyl and in which the alpha carbon atom is unsubstituted and the beta carbon atom is hydroxyl substituted.

7. A method according to claim 6 in which $R_3$ and $R_4$ are each monohydroxyalkyl or dihydroxyalkyl of 2 to about 6 carbon atoms and in which the alpha carbon atom is unsubstituted and the beta carbon atom is hydroxyl substituted.

8. A method according to claim 1 in which $R_1$ and $R_2$ are each 2-hydroxyalkyl.

9. A method according to claim 1 in which $R_1$, $R_2$, $R_3$ and $R_4$ are each 2-hydroxyalkyl.

10. A method according to claim 1 in which $R_1$, $R_2$, $R_3$ and $R_4$ are each 2-hydroxyethyl.

11. A method according to claim 1 in which $R_1$, $R_2$, $R_3$ and $R_4$ are each 2-hydroxybutyl.

12. A method according to claim 1 in which said compound is contained in a wound dressing.

13. A method according to claim 1 in which said compound is contained in an ointment.

14. A wound dressing comprising a bandage having applied thereto a composition comprising a compound of the formula (I)

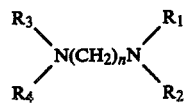

wherein:
 $R_1$ and $R_2$ may be the same or different and each is a substituted alkyl radical containing from 2 to about 6 carbon atoms and in which the substituents include one or more hydroxyl groups attached to carbon atoms other than the alpha carbon atom,
 $R_3$ and $R_4$ may be the same or different and each is an alkyl or substituted alkyl radical containing from one to about 6 carbon atoms, and
 n is from 2 to about 6.

15. A wound dressing according to claim 14 with the proviso that n is from 3 to about 6 when $R_1=R_2=R_3=R_4$ and each is 2-hydroxypropyl.

16. A wound dressing according to claim 14 wherein n is from 3 to about 6.

17. A wound dressing according to claim 14 wherein n is 3 or 4.

18. A wound dressing according to claim 14 with the proviso that $R_1$ and $R_2$ contain a maximum of 3 carbon atoms when no hydroxyl group is present.

19. A wound dressing according to claim 14 in which $R_1$ and $R_2$ are each monohydroxyalkyl or dihydroxyalkyl and in which the alpha carbon atom is unsubstituted and the beta carbon atom is hydroxyl substituted.

20. A wound dressing according to claim 19 in which $R_3$ and $R_4$ are each monohydroxyalkyl or dihydroxyalkyl of 2 to about 6 carbon atoms and in which the alpha carbon atom is unsubstituted and the beta carbon atom is hydroxyl substituted.

21. A wound dressing according to claim 14 in which $R_1$ and $R_2$ are each 2-hydroxyalkyl.

22. A wound dressing according to claim 14 in which $R_1$, $R_2$, $R_3$ and $R_4$ are each 2-hydroxyalkyl.

23. A wound dressing according to claim 14 in which $R_1$, $R_2$, $R_3$ and $R_4$ are each 2-hydroxyethyl.

24. A wound dressing according to claim 14 in which $R_1$, $R_2$, $R_3$ and $R_4$ are each 2-hydroxybutyl.

25. A pharmaceutical preparation for stimulating macrophage cell activity comprising a pharmaceutically effective amount of a monomeric compound of the formula (I)

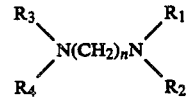

wherein:
 $R_1$ and $R_2$ may be the same or different and each is a substituted alkyl radical containing from 2 to about 6 carbon atoms and in which the substituents include one or more hydroxyl groups attached to carbon atoms other than the alpha carbon atom,
 $R_3$ and $R_4$ may be the same or different and each is an alkyl or substituted alkyl radical containing from one to about 6 carbon atoms, and
 n is from 2 to about 6, and a pharmaceutically acceptable carrier, said carrier being an ointment.

26. A pharmaceutical preparation according to claim 25 in which $R_1$, $R_2$, $R_3$ and $R_4$ are each monohydroxyalkyl or dihydroxyalkyl and in which the alpha carbon atom is unsubstituted and the beta carbon atom is hydroxyl substituted.

27. A pharmaceutical preparation according to claim 26 in which $R_1$, $R_2$, $R_3$ and $R_4$ are each dihydroxyalkyl.

28. A pharmaceutical preparation according to claim 25 wherein n is from 3 to about 6.

* * * * *